(12) United States Patent
Atkin et al.

(10) Patent No.: US 9,974,735 B2
(45) Date of Patent: May 22, 2018

(54) DEPILATORY COMPOSITIONS

(71) Applicant: Reckitt & Colman (Overseas) Limited, Slough (GB)

(72) Inventors: Neil Atkin, Hull (GB); Samuel Dawson, Hull (GB); Jane Evison, Hull (GB); Fiona Kennedy, Hull (GB); Anne Tindal, Hull (GB); Haydn Ward, Hull (GB); Jane Warwick, Hull (GB)

(73) Assignee: RECKITT & COLMAN (OVERSEAS) LIMITED, Slough (GB)

( * ) Notice: Subject to any disclaimer, the term of this patent is extended or adjusted under 35 U.S.C. 154(b) by 0 days. days.

(21) Appl. No.: 15/498,070

(22) Filed: Apr. 26, 2017

(65) Prior Publication Data
US 2017/0224610 A1    Aug. 10, 2017

Related U.S. Application Data

(62) Division of application No. 14/395,677, filed as application No. PCT/GB2013/051064 on Apr. 26, 2013, now abandoned.

(30) Foreign Application Priority Data

Apr. 26, 2012   (GB) .................................. 1207493.6

(51) Int. Cl.
| | |
|---|---|
| *A61K 8/46* | (2006.01) |
| *A61Q 9/04* | (2006.01) |
| *A61K 8/97* | (2017.01) |
| *A61K 8/25* | (2006.01) |
| *A61K 8/365* | (2006.01) |
| *A61K 8/19* | (2006.01) |
| *A61K 8/34* | (2006.01) |
| *A61K 8/29* | (2006.01) |
| *A61K 8/92* | (2006.01) |
| *A61K 8/86* | (2006.01) |
| *A61K 8/81* | (2006.01) |
| *A61K 8/42* | (2006.01) |

(52) U.S. Cl.
CPC .................. *A61K 8/97* (2013.01); *A61K 8/19* (2013.01); *A61K 8/25* (2013.01); *A61K 8/29* (2013.01); *A61K 8/342* (2013.01); *A61K 8/345* (2013.01); *A61K 8/365* (2013.01); *A61K 8/42* (2013.01); *A61K 8/8152* (2013.01); *A61K 8/8182* (2013.01); *A61K 8/86* (2013.01); *A61K 8/92* (2013.01); *A61Q 9/04* (2013.01); *A61K 2800/805* (2013.01)

(58) Field of Classification Search
CPC .......... A61Q 9/04; A61Q 19/00; A61Q 15/00; A61Q 11/00; A61Q 17/04; A61Q 19/004; A61Q 19/02; A61Q 19/04; A61Q 1/02; A61Q 1/04; A61Q 1/10; A61Q 19/08; A61Q 19/10; A61Q 5/04; A61Q 9/02; A61K 8/25; A61K 8/31; A61K 8/365; A61K 8/891; A61K 2800/242; A61K 2800/87; A61K 8/046; A61K 8/342; A61K 8/345; A61K 8/35; A61K 8/375; A61K 8/39; A61K 8/42; A61K 8/46; A61K 8/585; A61K 8/731; A61K 8/88; A61K 8/892; A61K 8/92; A61K 2800/244; A61K 2800/412; A61K 8/0208; A61K 8/11; A61K 8/19; A61K 8/20; A61K 8/368; A61K 8/4946; A61K 8/4953; A61K 8/645; A61K 8/732; A61K 8/733; A61K 8/8147; A61K 8/8152; A61K 8/8194; A61K 8/86; A61K 8/896; A61K 9/0014

See application file for complete search history.

(56) References Cited

U.S. PATENT DOCUMENTS

| | | | | |
|---|---|---|---|---|
| 4,088,751 | A * | 5/1978 | Kenkare | A61K 8/4946 252/70 |
| 2005/0255134 | A1 | 11/2005 | Hasenzahl et al. | |
| 2007/0105977 | A1 | 5/2007 | Gabriel et al. | |
| 2007/0202185 | A1 * | 8/2007 | Amundson | A61K 8/0208 424/490 |
| 2009/0068119 | A1 * | 3/2009 | Cawthorne | A61K 8/046 424/47 |
| 2010/0083443 | A1 | 4/2010 | Tindal et al. | |

FOREIGN PATENT DOCUMENTS

| | | | |
|---|---|---|---|
| DE | 1198009 B | 8/1965 | |
| EP | 0096521 A2 | 12/1983 | |
| EP | 20096521 A2 * | 12/1983 | ............... A61K 8/73 |
| WO | 2005123022 A1 | 12/2005 | |
| WO | WO2005123022 A1 * | 12/2005 | ............ A61K 7/155 |
| WO | 2009090362 A1 | 7/2009 | |
| WO | WO2009090362 A1 * | 7/2009 | ............... A61K 8/73 |
| WO | 2010082024 A2 | 7/2010 | |

OTHER PUBLICATIONS

International Search Report in related application No. PCT/GB2013/051064 dated Aug. 20, 2014.
International Preliminary Report on Patentability in related application No. PCT/GB2013/051064 dated Oct. 28, 2014.

\* cited by examiner

*Primary Examiner* — Audrea Buckley
(74) *Attorney, Agent, or Firm* — Troutman Sanders LLP; Ryan Schneider; Chris Davis (57) ABSTRACT

The present invention is directed to a depilatory composition which comprises a depilatory active and at least one material which alters the thermal properties of the composition by either having a higher heat of fusion or a lower thermal conductivity than the bulk.

4 Claims, 8 Drawing Sheets

DEPILATORY COMPOSITIONS

CROSS-REFERENCE TO RELATED APPLICATIONS

This application is a divisional application of, and claims priority to, U.S. patent application Ser. No. 14/395,677, filed 20 Oct. 2014, which is the U.S. National Stage of International Application No. PCT/GB2013/051064, filed 26 Apr. 2013, which claims the benefit of GB 1207493.6, filed 26 Apr. 2012, all of which are herein fully incorporated by reference.

BACKGROUND OF THE INVENTION

The present invention is directed to depilatory compositions. In particular, the present invention is directed to a depilatory composition that comprises a material which enables the composition to retain heat for better hair removal efficacy.

BRIEF SUMMARY OF THE INVENTION

As specified in the Background Section, there is a great need in the art to identify technologies for improved depilatory compositions. The present invention satisfies this and other needs. Embodiments of the present invention relate generally to such depilatory compositions and more specifically to depilatory compositions that comprise a material which enables the composition to retain heat for better hair removal efficacy.

In one aspect, the invention provides a method of removing hair from skin comprising the steps of:

(a) applying heat to a depilatory composition which comprises a combination of components selected from the group consisting of saturated hydrocarbons, vinylpyrrolidone/hexadecane co-polymers, fatty acids, fatty alcohols, esters, and surfactants, which on heating act to enable the composition to have an improved cooling profile; and (b) applying the heated depilatory composition to an area of the skin.

In some embodiments, the depilatory composition is heated to a temperature of 40° C.-60° C. In other embodiments, the depilatory composition is heated to a temperature of 45° C.-55° C. In one specific embodiment, the depilatory composition is heated to a temperature of 55° C.

In one embodiment, the depilatory composition retains its heat for a period of up to 15 minutes. In another embodiment, the depilatory composition retains its heat for a period of up to 12 minutes.

In still another embodiment, the depilatory composition cools to a temperature of 32° C.-35° C. over a period of 10-15 minutes.

In one embodiment, the combination of components which on heating act to enable the depilatory composition to have an improved cooling profile is selected from the group consisting of cetearyl alcohol, ceteareth 20, and a copolymer of vinylpyrrolidone and hexadecane.

In another embodiment, the combination of components which on heating act to enable the depilatory composition to have an improved cooling profile is present at a level of at least 9%. In a further embodiment, the combination of components which on heating act to enable the composition to have an improved cooling profile is present at a level of 9.5-10%.

In another embodiment, the depilatory composition further comprises a depilatory active and at least one material which alters the thermal properties of the depilatory composition by either having a higher heat of fusion or a lower thermal conductivity than the bulk.

In a further embodiment, the at least one material which alters the thermal properties of the depilatory composition is selected from the group consisting of a phase changing material, a micro-encapsulated phase changing material, a silica-based insulator, and a silicate-based insulator. In one embodiment, the phase changing material is selected from the group consisting of organic materials, inorganic materials, and mixtures thereof. In another embodiment, the phase changing material is selected from the group consisting of a mixture of saturated hydrocarbons, fatty acids, fatty alcohols, and esters thereof. In yet another embodiment, the micro-encapsulated phase-changing material is selected from the group consisting of saturated hydrocarbons, fatty acids, fatty alcohols, fatty esters, and hydrated inorganic salts thereof. In a specific embodiment, the silica is selected from the group consisting of silica aerogels and fumed silica material. In another specific embodiment, the silicate-based insulator is selected from the group consisting of mica, clay, bentonite, and kaolin.

In a further embodiment, the depilatory active is selected from the group consisting of potassium thioglycolate, dithioetythritol, thioglycerol, thioglycol, thioxanthine, thiosalicylic acid, N-acetyl-L-cysteine, lipic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide, NaSH, KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate, and cysteamine, and combinations thereof.

In another embodiment, the depilatory composition further comprises talc, water, magnesium trisilicate, sodium gluconate, calcium hydroxide, sorbitol 70%, glycerin, TiO2/propylene glycol, mineral oil, cetearyl alcohol, ceteareth 20, lotus flower milk extract, acrylates copolymer, urea, lithium magnesium sodium silicate, potassium thioglycolate (TGK) 43% solution, a copolymer of vinylpyrrolidone and hexadecane, and potassium hydroxide solution 50%.

In another aspect, the invention provides a method of depilation comprising the steps of:

(a) applying heat to a depilatory composition which comprises a depilatory active and at least one material which alters the thermal properties of the depilatory composition by either having a higher heat of fusion or a lower thermal conductivity than the bulk; and (b) applying the heated depilatory composition to an area of skin.

In one embodiment, the at least one material which alters the thermal properties of the depilatory composition is selected from the group consisting of a phase changing material, a micro-encapsulated phase changing material, a silica-based insulator, and a silicate-based insulator. In one embodiment, the phase changing material is selected from the group consisting of organic materials, inorganic materials, and mixtures thereof. In another embodiment, the phase changing material is selected from the group consisting of a mixture of saturated hydrocarbons, fatty acids, fatty alcohols, and esters thereof. In yet another embodiment, the micro-encapsulated phase-changing material is selected from the group consisting of saturated hydrocarbons, fatty acids, fatty alcohols, fatty esters, and hydrated inorganic salts thereof. In a specific embodiment, the silica is selected from the group consisting of silica aerogels and fumed silica material. In another specific embodiment, the silicate-based insulator is selected from the group consisting of mica, clay, bentonite, and kaolin.

In a further embodiment, the depilatory active is selected from the group consisting of potassium thioglycolate, dithioetythritol, thioglycerol, thioglycol, thioxanthine, thiosalicylic acid, N-acetyl-L-cysteine, lipic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide, NaSH, KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate, and cysteamine, and combinations thereof.

In another embodiment, the depilatory composition further comprises talc, water, magnesium trisilicate, sodium gluconate, calcium hydroxide, sorbitol 70%, glycerin, $TiO_2$/propylene glycol, mineral oil, cetearyl alcohol, ceteareth 20, lotus flower milk extract, acrylates copolymer, urea, lithium magnesium sodium silicate, potassium thioglycolate (TGK) 43% solution, a copolymer of vinylpyrrolidone and hexadecane, and potassium hydroxide solution 50%.

In some embodiments, the depilatory composition is heated to a temperature of 40° C.-60° C. In other embodiments, the depilatory composition is heated to a temperature of 45° C.-55° C. In one specific embodiment, the depilatory composition is heated to a temperature of 55° C.

In one embodiment, the depilatory composition retains its heat for a period of up to 15 minutes. In another embodiment, the depilatory composition retains its heat for a period of up to 12 minutes.

In still another embodiment, the depilatory composition cools to a temperature of 32° C.-35° C. over a period of 10-15 minutes.

In one embodiment, the depilatory composition further comprises a combination of components which on heating act to enable the depilatory composition to have an improved cooling profile, wherein the combination of components which on heating act to enable the composition to have an improved cooling profile is selected from the group consisting of saturated hydrocarbons, vinylpyrrolidone/hexadecane co-polymers, fatty acids, fatty alcohols, esters, and surfactants. In another embodiment, the combination of components which on heating act to enable the depilatory composition to have an improved cooling profile is selected from the group consisting of cetearyl alcohol, ceteareth 20, and a copolymer of vinylpyrrolidone and hexadecane.

In another embodiment, the combination of components which on heating act to enable the depilatory composition to have an improved cooling profile is present at a level of at least 9%. In a further embodiment, the combination of components which on heating act to enable the depilatory composition to have an improved cooling profile is present at a level of 9.5-10%.

These and other objects, features and advantages of the present invention will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below.

DETAILED DESCRIPTION OF THE INVENTION

As specified in the Background Section, there is a great need in the art to identify technologies for improved depilatory compositions. The present invention satisfies this and other needs. Embodiments of the present invention relate generally to such depilatory compositions and more specifically to depilatory compositions that comprise a material which enables the composition to retain heat for better hair removal efficacy.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

Compositions and Methods of the Invention

Currently, in order to achieve complete hair removal depilatory creams must be applied to a user's skin and left for a period of up to 10 minutes prior to removal.

According to a first aspect of the present invention, there is provided a depilatory composition which comprises a depilatory active and a material which alters the thermal properties of the composition by either having a higher heat of fusion or a lower thermal conductivity than the bulk.

The material can be in the form of a phase changing material, a micro-encapsulated phase changing material, or a silica or silicate-based insulator.

The phase changing material can be selected from organic, inorganic materials or mixtures thereof.

Typically, the phase changing material is selected from the group consisting of a mixture of saturated hydrocarbons, fatty acids, fatty alcohols or esters thereof. The encapsulated phase-changing material can be based on these materials and encapsulated in a suitable polymer shell, encapsulated phase change materials can be selected from saturated hydrocarbons, fatty acids, fatty alcohols, fatty esters or hydrated inorganic salts.

Non-limiting examples of suitable saturated hydrocarbons include paraffin waxes with formula $CH_3$—$(CH_2)n$-$CH_3$ where n=17 to 25.

Non-limiting examples of suitable non-paraffin organic materials include Lauryl bromide, Cetyl alcohol, Stearyl alcohol, Palmatic acid, Pentadecanoic acid, Lauric acid.

The silica-based insulator can be selected from silica aerogels or fumed silica. Silicate-based materials can be selected from a mica, a clay such as bentonite or kaolin.

The composition can further include a co-polymer, such as vinyl pyrrolidone/hexadecene co-polymer.

The composition can be in the form of a cream, lotion or a gel.

The depilatory composition may contain a skin-feel enhancing agent selected from at least one of silicone wax, talc and polyamide resin in the depilatory cream composition. In particular, the silicone wax, talc and/or a polyamide resin impart(s) a soft and velvety after-feel to the depilatory cream composition without affecting the composition's hair removal properties.

Talc is particularly preferred over other minerals which have previously been used in cosmetics as it confers a powdery after-feel which is desirable. In addition, it does not alter the colour of the composition. The talc may be present in an amount of 0.1 to 10 weight %, preferably 0.2 to 5 weight %, more preferably 0.5 to 3 weight %. In one embodiment, the composition includes 1 to 2 weight % talc.

The depilatory composition may further include a humectant. Suitable humectants include polyols, such as glycerine, propylene glycol and butylene glycol. Glycerine is preferred. The humectant may be present in an amount of 0 to 10 weight %, preferably 0.5 to 5 weight %.

The composition may comprise a polyamide resin as an alternative or in addition to the mineral. The polyamide resin may be present in an amount of 0.1 to 10 weight %, preferably 0.5 to 5 weight %, more preferably 1 to 3 weight %, for example 2 weight %. The polyamide resin is preferably Nylon-12.

The composition may also comprise a silicone wax as an alternative or in addition to the mineral and/or polyamide resin. Suitable silicone waxes include $C_{30}$-$C_{45}$ alkyl methicone and a silicone wax formed from stearoxytrimethylsilane and stearyl alcohol. The silicone wax is preferably $C_{30}$-$C_{45}$ alkyl methicone.

The silicone wax may be present in an amount of 0.1 to 10 weight %, preferably 0.5 to 5 weight %, more preferably 1 to 3 weight %, for example 1 to 2 weight %.

The emollient is selected from at least one of mineral oil, silicone and emollient esters. Together with the silicone wax, mineral and/or polyamide resin (and optional humectant), the emollient plays an important role in providing the depilatory cream composition with its desired skin-feel characteristics.

The emollient may be present in an amount of 1 to 10 weight %, preferably 3 to 7 weight % of the composition.

Mineral oil may be present in an amount of 0 to 10 weight %, preferably 0.5 to 5 weight % of the composition.

Silicone oil may be present in an amount of 0 to 10 weight %, preferably 0.5 to 5 weight %, for example 1 to 4 weight % of the composition.

Emollient esters may be present in an amount of 0 to 10 weight %, preferably 0.5 to 5 weight % of the composition, for example 1 to 3 weight %.

It is possible for the emollient to consist essentially of mineral oil. For example, in one embodiment, the composition includes talc and an emollient that consists essentially of mineral oil. In this embodiment, the emollient is present in an amount of 3 to 6 weight %, preferably 5 weight %. The talc is present in an amount of 0.3 to 1 weight %, preferably 0.5 weight %. Where an emollient consisting essentially of mineral oil emollient is employed, the composition preferably includes a humectant, such as glycerine.

It is also possible for the emollient to comprise or consist essentially of silicone oil(s). Preferably, a combination of silicone oils are present. The silicone oil may include at least one of cyclopentasiloxane, dimethiconol and dimethicone. Preferably, the silicone oil comprises cyclopentasiloxane, dimethiconol and dimethicone. The silicone oil may include 0.1 to 5 weight %, preferably 1 to 2 weight % dimethicone; and/or 1 to 5 weight %, for example, 1 to 3 weight % cyclopentasiloxane and dimethiconol.

It is possible for the emollient to consist essentially of an emollient ester. However, the emollient ester is preferably used in combination with a mineral oil and/or a silicone oil.

In one embodiment, the emollient comprises at least two of mineral oil, silicone oil and emollient esters. For example, the emollient may include mineral oil and silicone oil, or mineral oil and emollient esters, or silicone oil and emollient esters. In one embodiment, the emollient includes mineral oil, silicone oil and emollient esters.

Any suitable silicone oil may be employed. Examples include cyclopentasiloxane, dimethiconol and dimethicone. The total amount of silicone oil in the composition may be 0.1 to 10 weight %, for example, 2 to 5 weight %.

Any suitable emollient ester may be employed. Suitable examples include isopropyl palmitate, isopropyl myristate, myristyl lactate, cetyl esters, isotridecyl isononanoate, $C_{12\text{-}15}$ alkyl benzoate, caprylic/capric triglyceride and pentaerythrityl tetraisostearate.

In one embodiment, the emollient comprises mineral oil. The mineral oil may be present in an amount of 3 to 6 weight %, preferably 5 weight %. In a preferred embodiment, this combination of emollients is used together with at least one of talc and polyamide resin.

The depilatory active is a compound capable of degrading keratin and may be, for example, a sulphur compound such as potassium thioglycolate, dithioetythritol, thioglycerol, thioglycol, thioxanthine, thiosalicylic acid, N-acetyl-L-cysteine, lipic acid, $NaHSO_3$, $Li_2S$, $Na_2S$, $K_2S$, MgS, CaS, SrS, BaS, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and/or cysteamine. However, the composition is preferably substantially or, more preferably, is completely free from depilatory agents that destroy the thermodynamic equilibrium or the surface tension of the composition; examples of such agents include alkali metal sulphides.

Preferred depilatory compounds are thioglycolates, or their precursor thioglycolic acid. Most preferred is potassium thioglycolate, which may be produced by mixing thioglycolic acid with a neutralising source of potassium hydroxide (as noted above excess potassium hydroxide over that required to effect neutralisation cannot be used).

The depilatory active may be present in an amount of 2 to 25 weight %, preferably 5 to 20 weight %, more preferably 10 to 15 weight %. In one embodiment, the composition includes potassium thioglycolate in an amount of 2 to 25 weight %, preferably 5 to 20 weight %, more preferably 10 to 15 weight %.

The depilatory composition of the present invention preferably includes water. Water may be present in an amount of at least 40 weight %, preferably at least 50 weight %. Suitable amounts of water range from 40 to 70 weight %, preferably 50 to 65 weight %, more preferably 55 to 60 weight %.

The depilatory composition may optionally include one or more surfactant(s). The surfactant may be anionic, cationic or non-ionic. It is preferably non-ionic. Examples of suitable surfactants include cetearyl phosphate, cetearyl alcohol, cetearyl glucoside, cetostearyl alcohol and/or ceteareth 20. It is preferably present in an amount of from 0.5 to 15 wt % relative to the weight of the depilatory composition, more preferably from 1 to 10 wt %.

The depilatory composition can be provided with a combination of components selected from saturated hydrocarbons, vinylpyrrolidone/hexadecane co-polymer, fatty acids, fatty alcohols, esters and surfactants which on heating act to enable the composition to have an improved cooling profile.

The depilatory combination can include a combination of cetearyl alcohol, ceteareth 20 and a copolymer of vinylpyrrolidone and hexadecane. Typically, this preferred combination is present at a level of at least 9%. More typically, the preferred combination is present at a level of at 9.5-10%.

The depilatory composition may optionally include a source of alkalinity. This may include hydroxides, such as hydroxides of alkali and alkaline earth metals. Suitable hydroxides include sodium hydroxide, potassium hydroxide, calcium hydroxide and magnesium hydroxide. Preferably, calcium hydroxide is employed, optionally together with potassium hydroxide. The source of alkalinity (e.g. calcium hydroxide) may be present in an amount of 0.1 to 10 weight %, preferably 1 to 6 weight %, for example 2 to 5 weight % of the depilatory cream composition.

The depilatory composition preferably has a pH of greater than 7, for example, 9 to 12.5.

Optionally, the composition includes an accelerator that will accelerate the hair removal reaction. Examples of such accelerators include urea, thiourea, dimethyl, isosorbide (DMI), ethoxydiglycol (Transcutol) or methyl propyl diol (MP diol). Preferably the accelerator is urea. The composition according to the invention preferably comprises from 5% to 15% wt, more preferably from 6 to 10 wt % of an accelerator (e.g. urea).

The depilatory composition may comprise other optional ingredients, such as pigments and fillers, such as clays. Examples of suitable clays include sodium magnesium silicate, magnesium trisilicate and titanium dioxide. The inclusion of a clay, preferably sodium magnesium silicate, more preferably in an amount of from 0.1 to 10 wt % relative to the weight of the depilatory composition, most preferably from 0.1 to 1 wt %, is particularly advantageous, since this provides sodium and magnesium ions for the buffer system and improves the efficiency of depilation.

The depilatory cream composition desirably includes a chelating agent, such as sodium gluconate. The chelating agent may be present in an amount of less than 1 weight %, preferably 0.01 to 0.5 weight %, for example 0.05 to 0.1 weight %.

The depilatory cream composition may also include an additive that prevents phase separation. Suitable additives include polymers or copolymers of acrylic acid, for example, an acrylate copolymer. Such additives may be present in an amount of up to 2 weight %, preferably less than 1 weight %, more preferably less than 0.5 weight %, for example 0.1 to 0.4 weight %.

Optionally, additives such as aloe vera, lotus flower milk and Vitamin E may also be included in the composition. Such additives are employed in amounts of less than 1 weight %, for example, 0.1 to 0.5 weight % of the composition.

The composition can be in the form of a base cream, an aerosol cream or a shower cream.

Typically the residence time is less than 10 minutes, more preferably not more than 6 minutes, even. Very suitably the residence time is 1 to 5 minutes, about 2 to 3 minutes being especially preferred.

According to a second aspect of the present invention, there is provided a method of removing hair from the skin comprising the steps of (a) applying heat to a depilatory composition which comprises a combination of components selected from saturated hydrocarbons, vinylpyrrolidone/hexadecane co-polymer, fatty acids, fatty alcohols, esters and surfactants which on heating act to enable the composition to have an improved cooling profile; and (b) applying said heated depilatory composition to an area of the skin.

Typically the depilatory composition is heated to a temperature of 40° C.-60° C. More typically, the temperature is 45° C.-55° C. Most typically, the temperature is 55° C.

The depilatory composition can retain its heat for a period of up to 15 minutes. Typically, the depilatory composition can retain its heat for a period of up to 12 minutes.

The depilatory composition cools to a temperature of 32° C.-35° C. over a period of 10-15 minutes.

A preferred combination is cetearyl alcohol, ceteareth 20 and a copolymer of vinylpyrrolidone and hexadecane. Typically, this preferred combination is present at a level of at least 9%. More typically, the preferred combination is present at a level of at 9.5-10%.

According to a third aspect of the present invention, there is provided a use of a heated depilatory composition which comprises a combination of components selected from saturated hydrocarbons, vinylpyrrolidone/hexadecane co-polymer, fatty acids, fatty alcohols, esters and surfactants which on heating act to enable the composition to have an improved cooling profile for the removal of hair from the skin Typically the depilatory composition is heated to a temperature of 40° C.-60° C. More typically, the temperature is 45° C.-55° C. Most typically, the temperature is 55° C.

The depilatory composition can retain its heat for a period of up to 15 minutes. Typically, the depilatory composition can retain its heat for a period of up to 12 minutes.

The depilatory composition cools to a temperature of 32° C.-35° C. over a period of 10-15 minutes.

A preferred combination is cetearyl alcohol, ceteareth 20 and a copolymer of vinylpyrrolidone and hexadecane. Typically, this preferred combination is present at a level of at least 9%. More typically, the preferred combination is present at a level of at 9.5-10%.

Examples

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here.

Example embodiments of the invention are shown in the table below:

| Standard Name | Ex 1 (%) | Ex 2 (%) | Ex 3 (%) | Ex 4 (%) | Ex 5 (%) | Ex 6 (%) | Ex 7 (%) | Ex 8 (%) |
| --- | --- | --- | --- | --- | --- | --- | --- | --- |
| Talc | 2.00 | 2.00 | 2.00 | 2.00 | 2.00 | 2.00 | 2.00 | 2.00 |
| Water | 42.555 | 42.555 | 42.555 | 57.455 | 56.55 | 56.55 | 57.455 | 55.21 |
| Magnesium Triscillicate | 0.50 | 0.50 | 0.50 | 0.50 | 0.50 | 0.50 | 0.50 | 0.50 |
| Sodium Gluconate | 0.10 | 0.10 | 0.10 | 0.10 | 0.10 | 0.10 | 0.10 | 0.10 |
| Calcium Hydroxide | 3.56 | 3.56 | 3.56 | 3.56 | 3.56 | 3.56 | 3.56 | 3.56 |

-continued

| Standard Name | Ex 1 (%) | Ex 2 (%) | Ex 3 (%) | Ex 4 (%) | Ex 5 (%) | Ex 6 (%) | Ex 7 (%) | Ex 8 (%) |
|---|---|---|---|---|---|---|---|---|
| Sorbitol 70% | 1.00 | 1.00 | 1.00 | 1.00 | 1.00 | 1.00 | 1.00 | 0.00 |
| Glycerin | 1.00 | 1.00 | 1.00 | 1.00 | 1.00 | 1.00 | 1.00 | 1.00 |
| TiO$_2$/Propylene Glycol | 0.60 | 0.60 | 0.60 | 0.60 | 0.60 | 0.60 | 0.60 | 0.60 |
| Thick Mineral Oil | 4.80 | 4.80 | 4.80 | 4.80 | 4.80 | 4.80 | 4.80 | 4.80 |
| Cetearyl Alcohol | 4.40 | 4.40 | 4.40 | 4.40 | 4.40 | 4.40 | 4.40 | 6.10 |
| Ceteareth 20 | 1.76 | 1.76 | 1.76 | 1.76 | 1.76 | 1.76 | 1.76 | 2.43 |
| VP/Hexadecene Co-polymer | 0.00 | 0.00 | 0.00 | 0.00 | 0.00 | 0.00 | 0.00 | 1.00 |
| PlusICE A46 | 15.00 | — | — | — | — | — | — | — |
| MPCM 43 D | — | 15.00 | — | — | — | — | — | — |
| Parafol 22-95 | — | — | 15.00 | — | — | — | — | — |
| VM-2270 Aerogel | — | — | — | 0.10 | — | — | — | — |
| VM-2270 Aerogel | — | — | — | — | 1.00 | — | — | — |
| Fumed Silica | — | — | — | — | — | 1.00 | 0.1 | — |
| Lotus Flower Milk Extract | 0.10 | 0.10 | 0.10 | 0.10 | 0.10 | 0.10 | 0.10 | 0.10 |
| Acrylates Copolymer | 0.10 | 0.10 | 0.10 | 0.10 | 0.10 | 0.10 | 0.10 | 0.10 |
| Urea | 8.00 | 8.00 | 8.00 | 8.00 | 8.00 | 8.00 | 8.00 | 8.00 |
| Lithium Magnesium Sodium Silicate | 0.20 | 0.20 | 0.20 | 0.20 | 0.20 | 0.20 | 0.20 | 0.20 |
| Spray Dried Silica | 0.025 | 0.025 | 0.025 | 0.025 | 0.025 | 0.025 | 0.025 | — |
| Thelma 200 Fragrance | 0.40 | 0.40 | 0.40 | 0.40 | 0.40 | 0.40 | 0.40 | — |
| Nutrifruit Fragrance | — | — | — | — | — | — | — | 0.40 |
| Potassium Thioglycolate (TGK) 43% solution | 12.90 | 12.90 | 12.90 | 12.90 | 12.90 | 12.90 | 12.90 | 12.90 |
| Potassium Hydroxide Solution 50% | 1.00 | 1.00 | 1.00 | 1.00 | 1.00 | 1.00 | 1.00 | 1.00 |
| Total | 100 | 100 | 100 | 100 | 100 | 100 | 100 | 100 |

The compositions can be formulated using standard techniques known to the man skilled in the art.

Phase changing materials (PCM) are compounds which melt and solidify at certain, specific temperatures. As the solid material is heated it absorbs energy, at melting point it absorbs a greater amount of energy which is stored until the material cools back below its melting point. As the temperature drops below the phase change materials melting point the stored energy is released. The amount of energy able to be stored is dependant of the PCM's latent heat capacity. These materials were exploited so that when the depilatory cream was warmed, heat was stored and then released once the cream was cooled down at the particular PCM's operating temperature range.

Aerogel is a material principally made from silica; an electrochemical separation process is used in its production to remove the liquid in silica gel and replace it with a gas. Aerogel is predominantly used for different applications including as a thickening agent in cosmetics and paints.

Fumed silica is made from the continuous flame hydrolysis of silicon tetrachloride. Fumed Silica is also used for its thickening properties in cosmetic and pharmaceuticals. This silica derivative should exhibit similar insulating properties to Aerogel.

Microencapsulated phase change materials (MPCMs) are phase change materials whereby the structure allows the MPCM to exist in the formulation without affecting the rest of the formulation. Due to the microencapsulation the MPCMs should have little to no effect on the creams viscosity or appearance.

Parafol is another example of a phase change wax that can be used. It has a particularly high latent heat capacity but does result in a significant reduction in viscosity of the final formulation when heated above 45° C.

Figure 1:
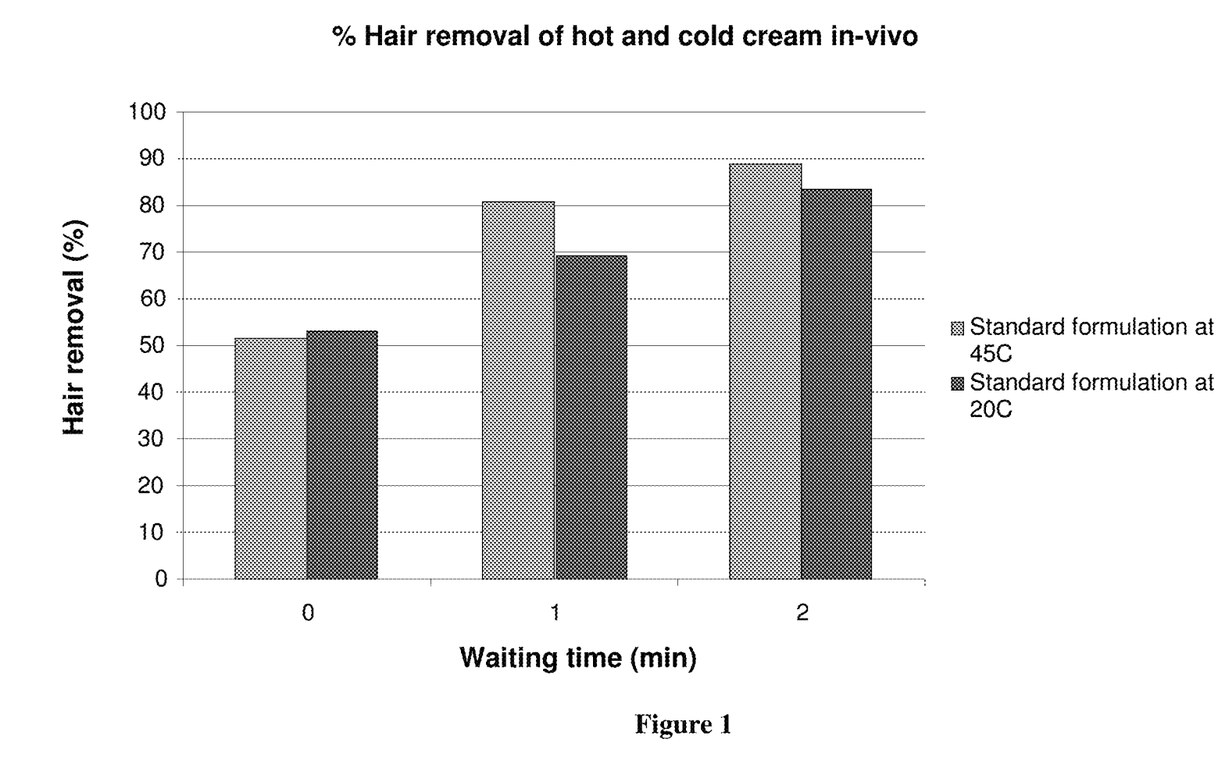
FIG. 1 illustrates a comparison of hair removal efficacy on consumers at different temperature with different removal times.

FIG. 1 illustrates that when a standard hot depilatory cream is applied to the legs, there was not a significant difference in hair removal efficacy compared to the cold cream. While not wishing to be bound by any theory, it is believed that this is because the hot cream cools down quickly on the leg, negating any benefits the heat would provide.

Figure 2:
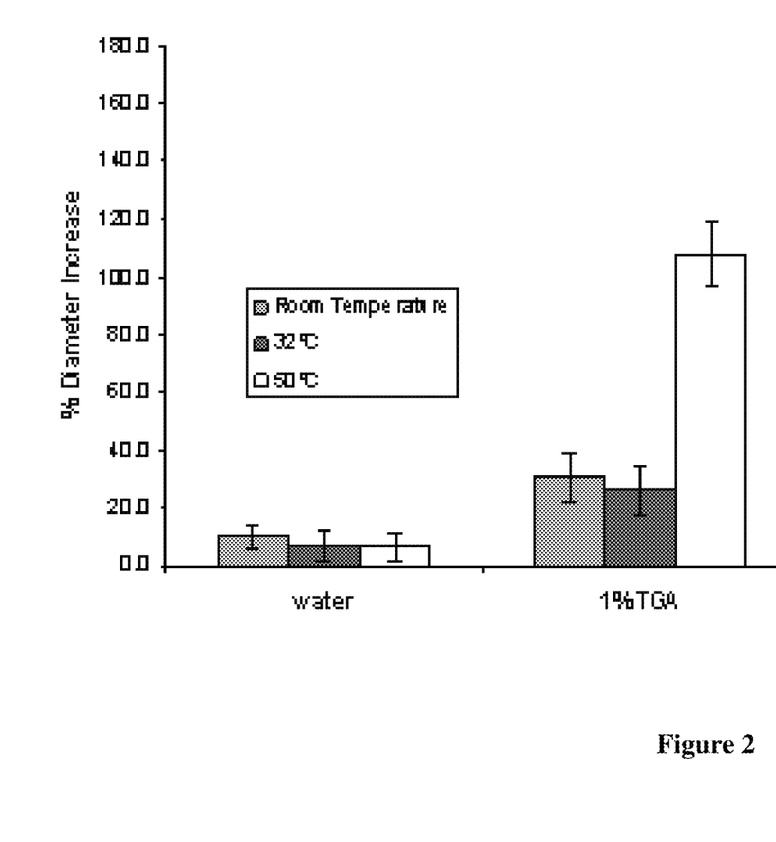
FIG. 2 illustrates hair swelling measurements at different temperatures after 1 minute.

A second in-vitro test looks at how quickly hairs swell. The amount of swelling is an indication of keratin damage and correlates to hair removal efficacy. The results, which are illustrated in FIG. 2, show that after 1 minute the hair swells more at 50° C. than at cooler temperatures. Therefore if the temperature of the cream can be maintained on the leg for around one minute the benefit of the heat should be seen in-vivo.

Testing Method
1. A water bath is switched on to operate at 54° C.
2. The creams to be tested are placed in the water bath to heat for a minimum of 30 minutes.

3. The temperature of the cream is checked frequently until it reaches the desired temperature.
4. A volunteer's arm is prepared by wrapping in cling film (to prevent any discomfort that might be caused to the volunteer once the heated cream is applied thereto).
5. Once the cream is at the desired temperature, an automated temperature logger is turned on and the cream is applied on the arm.
6. The automated logger records the temperature at 10 sec intervals for 3 minutes.
7. After 3 minutes the logger is switched off, the cream is removed, and the results are collected.

Figure 3:
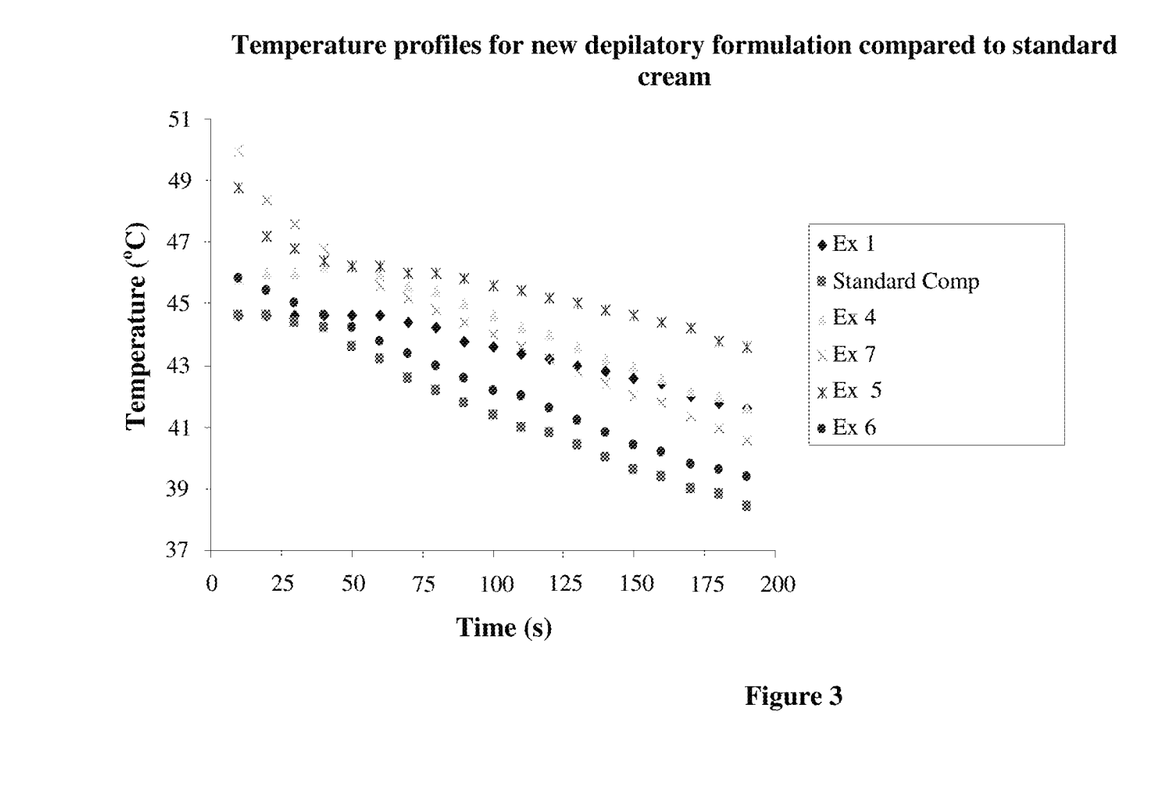
FIG. 3 illustrates the temperature profile of depilatory creams on the arm in an individual.

FIG. 3 shows that depilatory creams modified with either PCM or either of the silica slows the rate of cooling. Despite all creams being heated to the same amount, the temperature of the cream does vary from the initial measurement. This could be because some creams are losing heat rapidly in the first 10 seconds after application.

Figure 4:
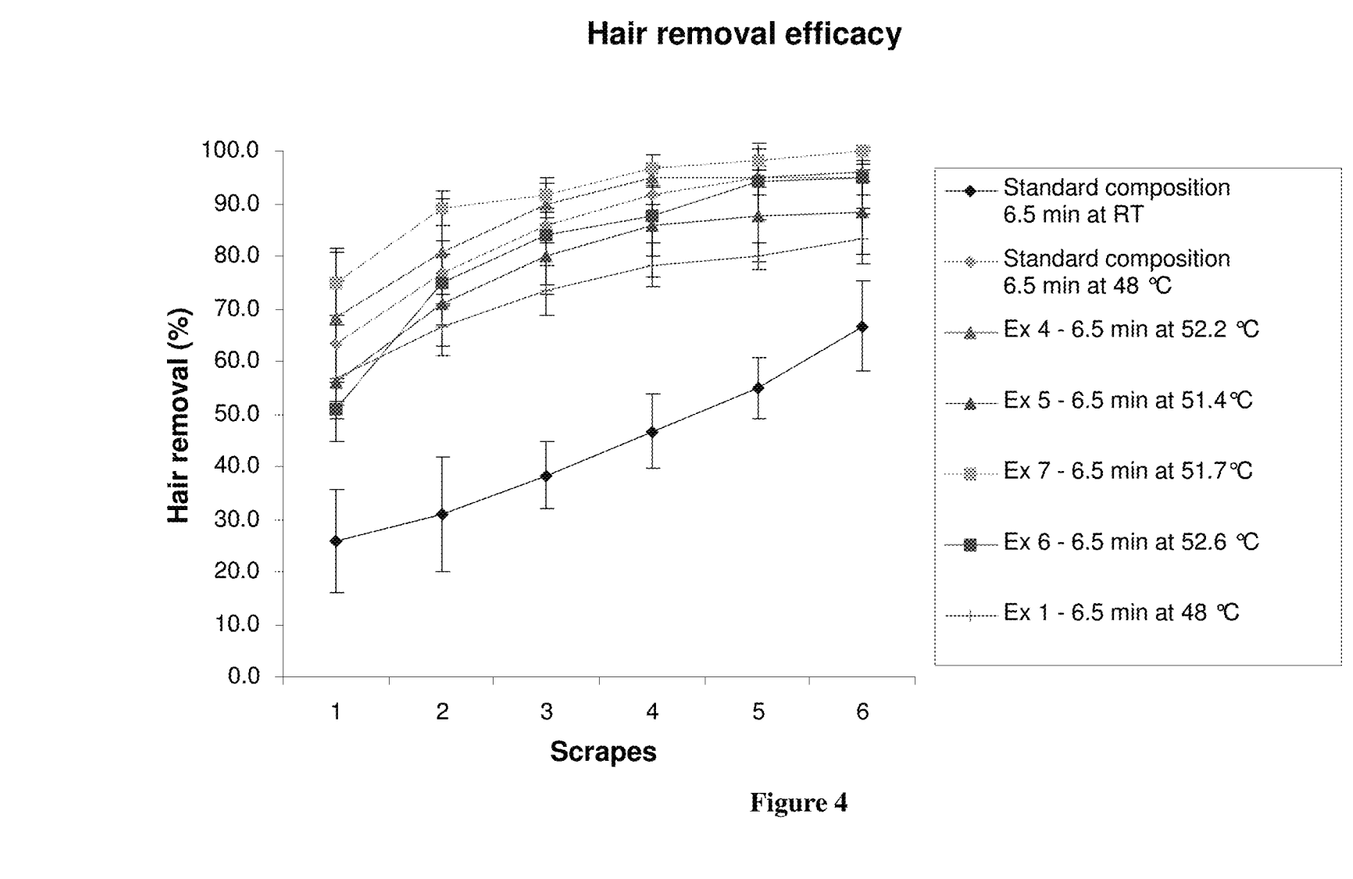
FIG. 4 illustrates hair removal efficacy from an in-vitro test method.

FIG. 4 shows all the heated creams removed hair much more effectively than the room temperature cream. There are differences between the heated creams, with a slight loss of efficacy at higher leaves of silica and with the PCM. Without being bound by theory, it is believed that this is because there is a larger proportion of non-aqueous matter in the formulation which does not directly contribute to the aqueous hair removal reaction.

TABLE 1

Effect of temperature on hair removal in-vitro.
Time for Complete Hair Removal

| Temperature (° C.) | Time (min) |
|---|---|
| 20 | 10 |
| 30 | 7 |
| 40 | 4 |
| 50 | 3 |

Table 1 above shows, using an in-vitro test, that an increase in temperature of the depilatory cream results in an increase in the rate of depilation.

Figure 5:
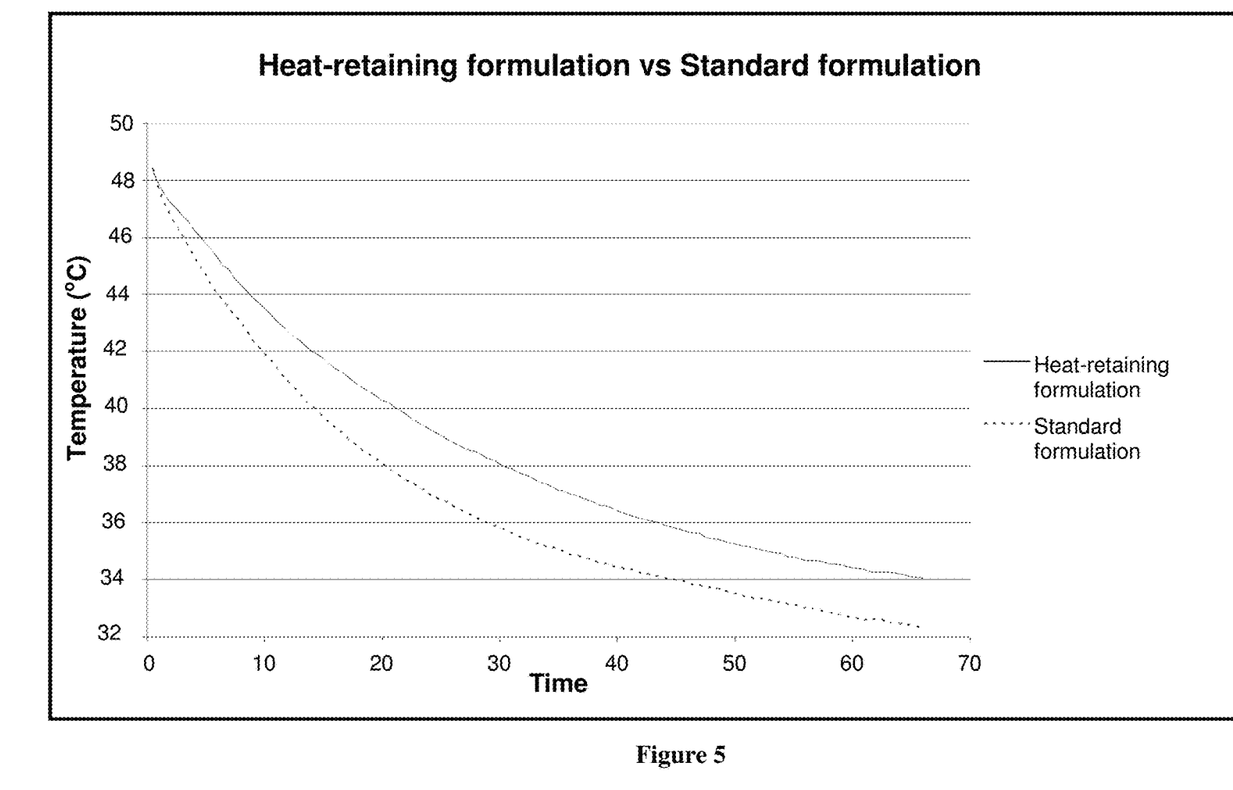
FIG. 5 illustrates the cooling profile of Example 8 in accordance with the present invention.
Figure 6:
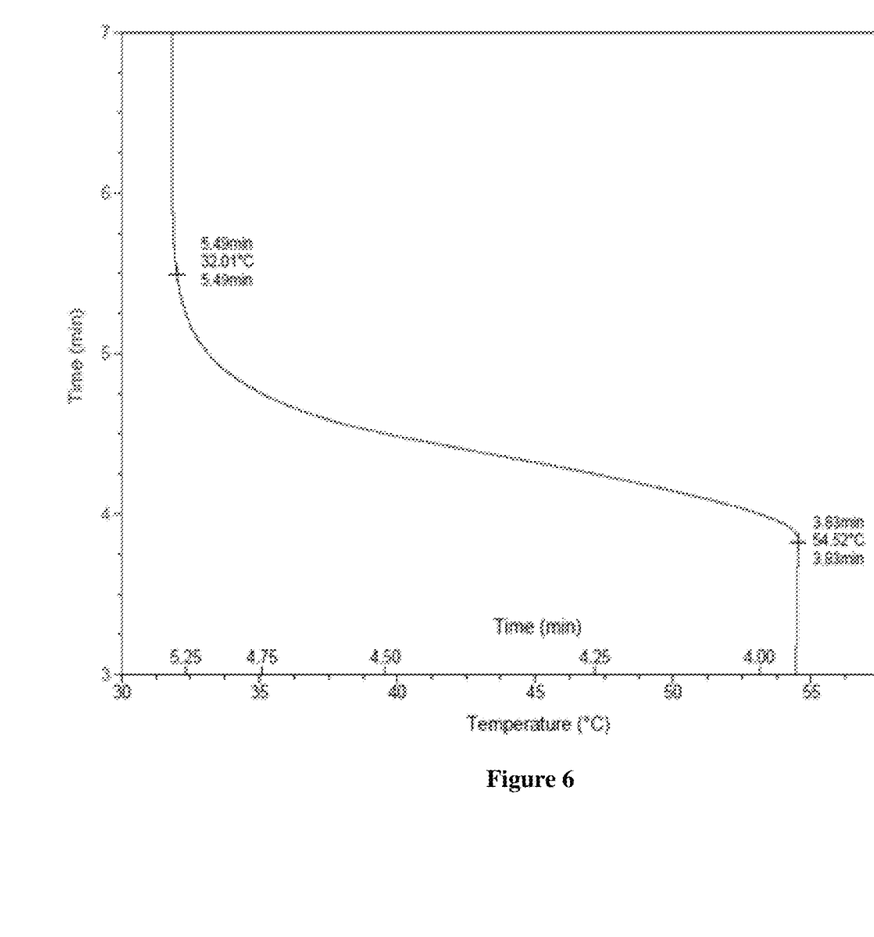
FIG. 6 illustrates the heat retention properties of Example 8 in accordance with the present invention.
Figure 7:
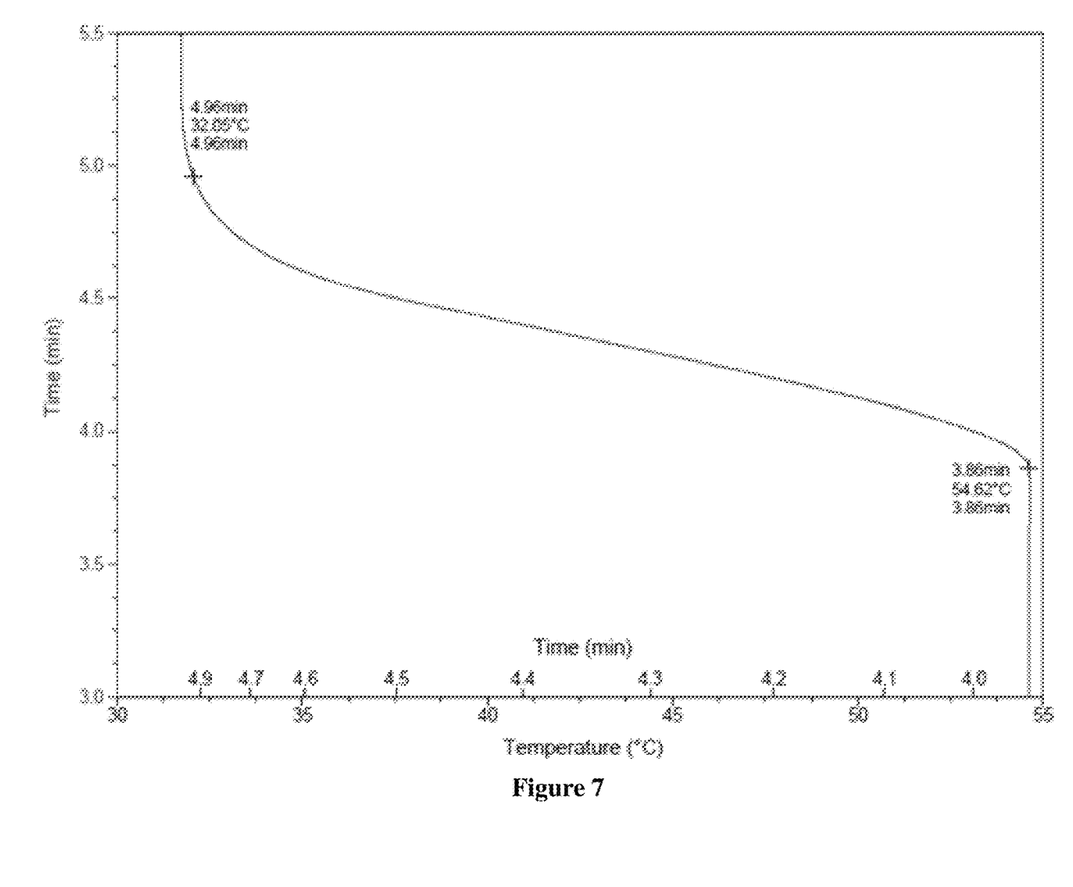
FIG. 7 illustrates the heat retention properties of a standard composition as a comparison.

FIGS. 5 and 6 illustrate the heat retention properties of Example 8. The results shown in these Figures demonstrate that the heat-retaining depilatory formulation which comprises a combination of components selected from vinylpyrrolidone/hexadecene co-polymer, saturated hydrocarbons, fatty acids, fatty alcohols, esters and surfactants retains heat for longer compared with a standard cream formulation that does not include this combination (FIG. 7).

Figure 8:
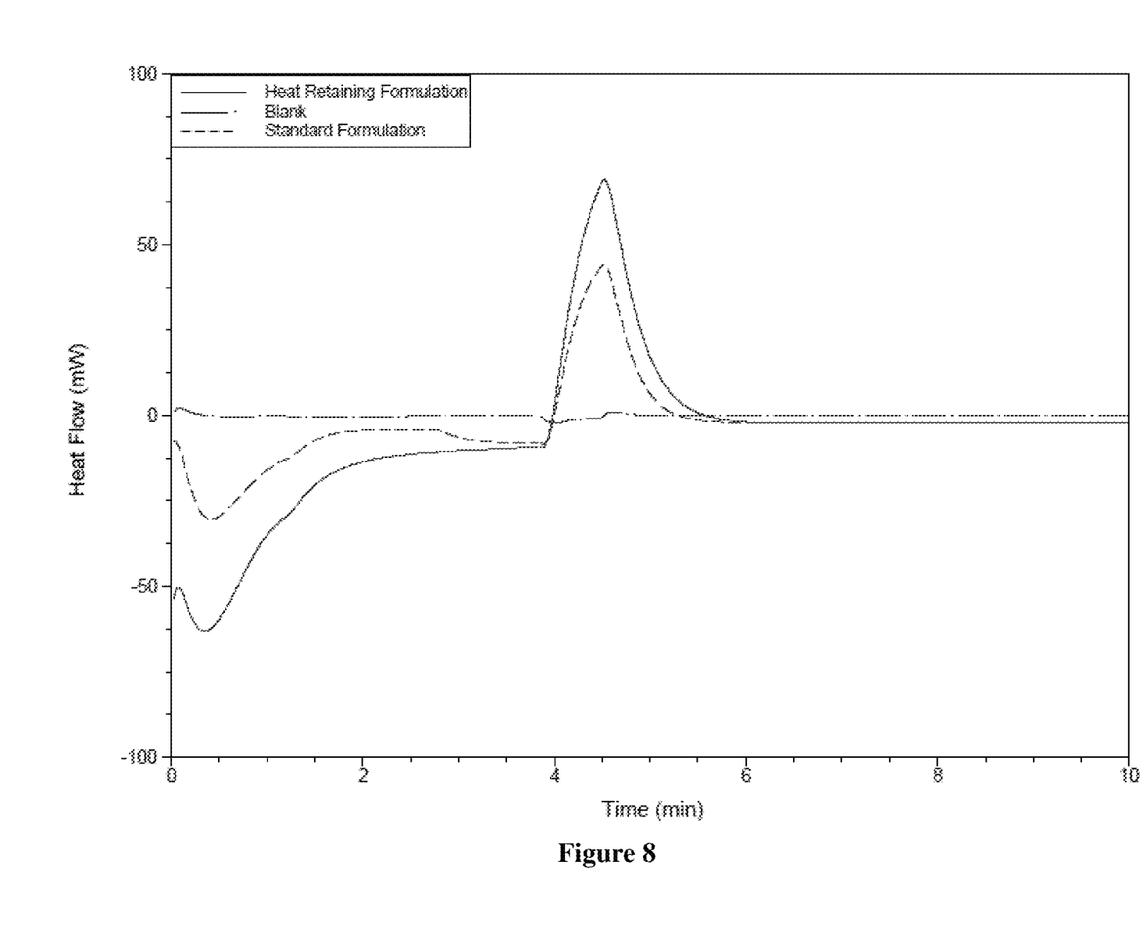
FIG. 8 illustrates an exotherm analysis of Example 8 in accordance with the present invention and a standard cream.

FIG. 8 illustrates an exotherm analysis which provides further support to the theory of better heat retention in the heated depilatory formulation. It shows the heat-retaining formulation emits the most heat on cooling and therefore is the slowest cooling.

An advantage of the present invention is that there is provided a depilatory cream whose efficacy is increased by pre-warming it. Additional advantages of the pre-warmed cream are based around the sensory feel it provides to the consumer.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present invention will be limited only by the appended claims and equivalents thereof. The scope of the invention is therefore indicated by the following claims, rather than the foregoing description and above-discussed embodiments, and all changes that come within the meaning and range of equivalents thereof are intended to be embraced therein.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

All patents, applications, publications, test methods, literature, and other materials cited herein are hereby incorporated by reference in their entirety as if physically present in this specification.

What is claimed is:

1. A method of removing hair from skin comprising the steps of:
    applying heat to a depilatory composition which comprises a depilatory active and at least one material which alters the thermal properties of the depilatory composition by either having a higher heat of fusion or a lower thermal conductivity than the depilatory composition,
    wherein the at least one material is in the form of a phase changing material or a microencapsulated phase changing material, and
    wherein the phase changing material comprises a mixture of cetearyl alcohol, ceteareth 20, and a copolymer of vinylpyrrolidone and hexadecene at a level of 9-10%;
    heating the depilatory composition to a temperature of 40° C.-60° C.; and
    applying the heated depilatory composition to an area of the skin,
    wherein the depilatory composition cools to a temperature of 32° C. to 35° C. over a period of 10-15 minutes, and
    wherein the at least one material acts on heating to enable the composition to have an improved cooling profile.

2. The method of removing hair from the skin as claimed in claim 1, wherein the depilatory composition retains its heat for a period of up to 15 minutes.

3. The method of removing hair from the skin as claimed in claim 1, wherein the at least one material is present at a level of at least 9%.

4. The method of depilation as claimed in claim 1, wherein the depilatory composition comprises talc, water, magnesium trisilicate, sodium gluconate, calcium hydroxide, sorbitol 70%, glycerin, TiO$_2$, propylene glycol, mineral oil, cetearyl alcohol, ceteareth 20, lotus flower milk extract, acrylates copolymer, urea, lithium magnesium sodium silicate, potassium thioglycolate (TGK) 43% solution, a copolymer of vinylpyrrolidone and hexadecane, and potassium hydroxide solution 50%.

\* \* \* \* \*